United States Patent [19]

Chang

[11] Patent Number: 4,816,396

[45] Date of Patent: * Mar. 28, 1989

[54] **METHOD AND VECTOR ORGANISM FOR CONTROLLED ACCUMULATION OF HETEROLOGOUS GENE PRODUCTS IN *BACILLUS SUBTILIS***

[75] Inventor: Shing Chang, Hercules, Calif.

[73] Assignee: Cetus Corporation, Emeryville, Calif.

[*] Notice: The portion of the term of this patent subsequent to Dec. 8, 2004 has been disclaimed.

[21] Appl. No.: 843,940

[22] Filed: Mar. 25, 1986

Related U.S. Application Data

[63] Continuation of Ser. No. 461,249, Jan. 26, 1983, abandoned, which is a continuation of Ser. No. 255,804, Apr. 20, 1981, abandoned, which is a continuation-in-part of Ser. No. 221,800, Dec. 31, 1981, abandoned, which is a continuation-in-part of Ser. No. 128,537, Mar. 10, 1980, abandoned.

[51] Int. Cl.$^4$ .................... C12P 21/00; C12N 15/00; C12N 1/20

[52] U.S. Cl. ................... 435/68; 435/172.1; 435/172.3; 435/252.31; 435/320; 935/29; 935/38; 935/39; 935/40; 935/41; 935/72; 935/74

[58] Field of Search ............ 435/68, 70, 91, 172.3, 435/253, 839, 172.1, 317.1, 320, 71, 243; 536/27; 935/38, 39, 40, 41, 29, 74

[56] References Cited

U.S. PATENT DOCUMENTS 4,237,224  12/1980  Cohen et al. .................... 435/172
4,431,740  2/1984  Bell et al. ......................... 435/68
4,711,843  12/1987  Chang ............................. 435/68

FOREIGN PATENT DOCUMENTS 2048894  12/1980  United Kingdom ............ 435/172.3

OTHER PUBLICATIONS

Lovett et al, "*Bacillus subtilis* as a Host for Molecular Cloning", Methods in Enzymology 68:342 (1979).

*Genes*, Lewin, John Wiley & Sons, New York, 1983, p. 673.

Gryczan et al, "Molecular Cloning of Heterologous Chromosomal DNA by Recombination Between a Plasmid Vector and a Homologous Resident Plasmid in *Bacillus subtilis*", Molec. Gen. Genet., 177:459 (1980).

Gryczan et al, "Characterization of Chimeric Plasmid Cloning Vehicles in *Bacillus subtilis*", J. Bacteriol., 141:246 (1980).

Ehrlich, "DNA Cloning in *Bacillus subtilis*", Proc. Natl. Acad. Sci. USA, 75:1433 (1978).

Gryczan et al, "Construction and Properties of Chimeric Plasmids in *Bacillus subtilis*", Proc. Natl. Acad. Sci. USA, 75:1428 (1978).

Duncan et al, "Transformation of *Bacillus subtilis* and *Escherichia coli* by a Hybrid Plasmid pCD1", Chem. Abstr., 86:185728k (1977), of Gene, 1:153 (1977).

Taniguchi et al, "Construction and Identification of a Bacterial Plasmid Containing the Human Fibroblast Inteferon Gene Sequence", Proc. Japan. Acad., 55, Ser. B: 464 (1979).

Gray and Chang, *J. Bacteriol.*, 145:422–428 (1981).

Hori and Osawa, *PNAs* (USA), 76:381–385 (1979).

Rubin et al., *Chem. Abstr.*, 93:146134p (1980).

Young et al., in Genetic Engineering, Chakrabarty (ed), CRC Press 1978, pp. 145–147.

Erlich, *Proc. Natl. Acad. Sci.* USA, 74:1680 (1977).

Kreft et al., *Chem Abstr.*, 89:103524r (1978).

Keggins et al., *Proc. Natl. Acad. Sci.* USA, 75:1423 (1978).

*Primary Examiner*—James Martinell
*Attorney, Agent, or Firm*—Elliott L. Fineman; Jane R. McLaughlin; Virginia H. Meyer

[57] ABSTRACT

The invention discloses a method and cloning vectors useful for the production of cloned heterologous gene products in *B. subtilis*. Use of the method and vector allows the host to produce the heterologous gene product as a single unfused peptide having no extraneous amino acids attached.

19 Claims, 2 Drawing Sheets

FIG. 1

| Met Ser Tyr Asn Leu Leu Gly Phe Leu Gln Arg Ser Ser Asn Phe Gln Cys Gln Lys Leu |
| ATG AGC TAC ACC TTG CTT GGA TTC CTA CAA AGA AGC AAT TTT CAG TGT CAG AAG CTC |

Leu Trp Gln Leu Asn Gly Arg Leu Glu Tyr Cys Leu Lys Asp Arg Met Asn Phe Asp Ile
CTG TGG CAA TGG AAT GGG AGG CTT GAA TAT TGC CTC AAG GAC AGG ATG AAC TTT GAC ATC

Pro Glu Glu Ile Lys Gln Leu Glu Gln Phe Gln Lys Glu Asp Ala Ala Leu Thr Ile Tyr
CCT GAG GAG ATT AAG CAG CTG CAG CAG TTC CAG AAG GAG GAC GCC GCA TTG ACC ATC TAT

Glu Met Leu Gln Asn Ile Phe Ala Ile Phe Arg Gln Asp Ser Ser Ser Thr Gly Trp Asn
GAG ATG CTC CAG AAC ATC TTT GCT ATT TTC AGA CAA GAT TCA TCT AGC ACT GGC TGG AAT

Glu Thr Ile Val Glu Val Leu Asn Leu Ala Asn Val Tyr His Gln Ile Asn His Leu Lys Thr
GAG ACT ATT GTT GAG AAC CTC CTG GCT AAT GTC TAT CAT CAG ATA ACC CAT CTG AAG ACA

Val Leu Glu Lys Glu Leu Lys Glu Lys Lys Asp Phe Thr Arg Gly Lys Leu Met Ser Ser Leu
GTC CTG GAA GAA AAA CTG GAG AAA GAA GAT TTC ACC AGG GGA AAA CTC ATG AGC AGT CTG

His Leu Lys Arg Tyr Tyr Gly Arg Ile Tyr His Thr Tyr Leu Lys Ala Lys Glu Tyr Ser His
CAC CTG AAA AGA TAT TAT GGG AGG ATT CTG CAT TAC CTG AAG GCC AAG GAG TAC AGT CAC

Cys Ala Trp Thr Ile Val Arg Val Glu Ile Leu Arg Asn Phe Tyr Phe Ile Asn Arg Leu
TGT GCC TGG ACC ATA GTC AGA GTG GAA ATC CTA AGG AAC TTT TAC TTC ATT AAC AGA CTT

Thr Gly Tyr Leu Arg Asn ***
ACA GGT TAC CTC CGA AAC TGA

FIG. 3  B. LICHENIFORMIS PEN P GENE (262 b.p.)

BETA LACTAMASE PROMOTER SEQUENCE:

```
     BamHI
GGATCCCCCCAATTCTCATGTTTGACAGCTTATCATC
GGTCATCATTTCCTTCCGAAAAAACGGTTGCATTTAAATCTTACATATGTAATACTTTCA
                                    Hinf
AAGACTACATTTGTAAGATTTGATGTTTGAGTCGGCTGAAAGATCGTACGTACCAATTAT
TGTTTCGTGATTGTTCAAGCCATAACACTGTAGGGATAGTGGAAAGAGTGCTTCATCTGG
                                                         BamHI
TTACGATCAATCAAATATTCAAACGGAGGGAGACGGGGATC
```

FIG. 2 B. LICHENIFORMIS PEN P GENE
BETA LACTAMASE PROMOTER SEQUENCE:

```
                                                            GAATTCTCATGTTTGACAGCTTATCATC
GGTCATCATTTCCTTCCGAAAAACGGTTGCATTTAAATCTTACATATGTAATACTTTCA
                              Hinf
AAGACTACATTTGTAAGATTTGATGTTTGAGTCGGCTGAAAGATCGTACGTACCAATTAT
TGTTTCGTGATTGTTCAAGCCATAACACTGTAGGGATAGTGGAAAAGAGTGCTTCATCTGG
TTACGATCAATCAAATATTCAAACGGAGGAGACGATTTTGATGAAATTATGGTTCAGTA
                                            fMet Lys Leu Trp Phe Ser T
                                                                    5
                                              SIGNAL PEPTIDE →
CTTTAAAAACTGAAAAAGGCTGCAGCAGTGTTGCTTTTCTCTTGCCGTCGCGCTTGCAGGAT
hr Leu Lys Leu Lys Ala Ala Val Leu Leu Phe Ser Cys Val Ala Leu Ala Gly
                    PstI                 15                           25
GCGCTAACAATCAAACGAATGCCTCGCAACCTGCCGAGAAGAATGAAAAGACGGAGATGA
ys Ala Asn Asn Gln Thr Asn Ala Ser Gln Pro Ala Glu Lys Asn Glu Lys Thr Glu Met L
              30              35                    40                    45
                              ← SIGNAL PEPTIDE | MATURE PROTEIN →
AAGATGATTTTGCAAAACTTGAGGAACAATTTGATGCAAAACTCGGGATCTTTGCATTGG
ys Asp Asp Phe Ala Lys Leu Glu Glu Gln Phe Asp Ala Lys Leu Gly Ile Phe Ala Leu A
        50                    55                    60                    65
ATACAGGTACAAACCGG......
sp Thr Gly Thr Asn Arg......
        70 AMINO ACIDS
```

METHOD AND VECTOR ORGANISM FOR CONTROLLED ACCUMULATION OF HETEROLOGOUS GENE PRODUCTS IN *BACILLUS SUBTILIS*

This application is a continuation application of application Ser. No. 461,249 filed Jan. 26, 1983, now abandoned, which in turn was a continuation application of application Ser. No. 255,804 filed Apr. 20, 1981, now abandoned, which in turn was a continuation-in-part of application Ser. No. 221,800, filed Dec. 31, 1981, now abandoned which in turn was a continuation-in-part of application Ser. No. 128,537, filed Mar. 10, 1980, now abandoned.

This invention relates to molecular biology and, more particularly, to the so-called art of recombinant DNA. Specifically, the invention relates to a method and a cloning vector for the production of cloned heterologous gene products in *Bacillus subtilis* as single unfused proteins.

The invention utilizes three unique genetically engineered plasmids. These organisms have been deposited with the American Type Culture Collection, Rockville, Md., 20852. They have been assigned ATCC numbers 31,776–31,778. ATCC number 31,776 has been assigned to plasmid pOG1196; number 31,777 has been assigned to plasmid pOG2165; and number 31,778 has been assigned to plasmid pOG2110. Applicant has directed that the plasmids be freely available to the general public upon the issuance of a United States patent.

As is well known, the particular sequence of amino acids in a given protein is determined in accordance with the code carried in the gene for that protein. In the process of translation by which proteins are formed from DNA, via messenger RNA (mRNA), groups of three nucleotides in the mRNA called codons, each place one of twenty possible amino acids at a corresponding position in the protein chain.

With the advent of recombinant DNA techniques, genetic changes may be made deliberately by the introduction of a predetermined nucleotide sequence, either synthesized or isolated from one strain or species, into the genetic makeup of another strain or species. The predetermined nucleotide sequence may be selected to cause the strain or species into which it is introduced to produce, as part of the translation process, the protein encoded by the predetermined nucleotide sequence. When the modified strain or species proceeds with the normal replication process, it also then duplicates the inserted sequence.

Recombinant DNA techniques involve isolating a suitable piece of a DNA chain (a cloning vector) and breaking or severing the two strands of DNA of the cloning vector at the desired location where the foreign DNA is to be inserted. To do this, particular types of proteins, called restriction enzymes, are typically used. Restriction enzymes will break the DNA at particular nucleotide sequences, although with some restriction enzymes the break may not necessarily occur at the same point on the two intertwined DNA strands. In such a case, if two different types of DNA are severed in a similar manner, the open ends will be complementary and will, under suitable conditions, stick together with the complementary ends lying side by side. They may then be linked together enzymatically (with ligase). This makes it possible to recombine two DNA segments from any source into a single DNA molecule.

Once the DNA vector has been isolated and the foreign piece inserted therein, the recombinant DNA is then placed into a suitable host organism. In order for the host organism to replicate the inserted DNA, it is necessary that the recombinant DNA be inserted into the host in such a way as to become part of its genetic system. Such insertion can occur in a variety of ways. For example, in the bacterium *Escherichia coli*, two convenient types of cloning vectors have been utilized. *E. coli* bacteria, in addition to the main DNA chain or chromosome, frequently have one or more independently replicating circular loops of DNA known as plasmids. Also, a certain type of virus known as a lambda bacteriophage (phage) is also capable of infecting *E. coli* and becoming part of its genetic system. Recombinant DNA techniques have included the use of a variety of plasmids or phages as cloning vectors. This involves the isolation of plasmids or phages from the bacteria, the breaking open of the isolated DNA by restriction enzymes, the insertion of a foreign or heterologous piece of DNA into the plasmid or phage, the restoration of the circular form of the plasmid or the phage structure, and the return of the plasmid or phage to the *E. coli* cell. Once in the host, the heterologous DNA is not only replicated from generation to generation, but also will produce the protein for which it codes if the proper reading frame and promoters exist.

Most recombinant work to date has been carried out with *E. coli*. Like all bacteria, *E. coli* is a prokaryotic cell which has, instead of a true nucleus, a single "naked" chromosome not surrounded by a nuclear membrane. Yeast, on the other hand, are eukaryotes since they contain a true nucleus. Man is also a eukaryote, although one quite distinct from yeast since the two eukaryotes diverged from a common ancestor more than 1.2 billion years ago. Because of the distinct differences between man and yeast, it is not surprising that the two organisms are separated by an evolutionary gap of more than 1.2 billion years. More surprising is the fact that bacterial species can be separated by a similar evolutionary gap. But indeed this is the case for *E. coli* and its distinct evolutionary cousin *B. subtilis*. The two claim a common ancestor prior to the time they diverged some 1.2 billion years ago. See Hori and Osawa, PNAS, (USA) 76:381–385 (1979).

Although certain general approaches to cloning genes in *E. coli* are applicable to other organisms, e.g. yeast and *B. subtilis*. *E. coli* plasmids are not usually capable of replication in *B. subtilis* and *E. coli* genes are not generally expressed in *B. subtilis*. This is due to the great evolutionary differences between the two bacterial species. *B. subtilis* is preferable to *E. coli* as a host organism because of a greater efficiency for plasmid mediated transformation in *B. subtilis* and because it is non-pathogenic. *B. subtilis* is also a fermentation organism used extensively in industry and therefore its management on an industrial scale is familiar. Although the laboratory *E. coli* strain is a non-pathogenic organism native to the intestines of man and higher animals, there is concern that it might become disease producing if genetically altered. *B. subtilis*, on the other hand, lives in the soil and have never been associated with any disease of plants or animals. Thus there is less likelihood that a genetic alteration in *B. subtilis* would lead to a disease state in man or animals or plants.

In co-pending application Ser. No. 221,800, the first successful production of heterologous gene products by *B. subtilis* is described. This represents a profound advance in genetic engineering. The present invention relates to an advance in the basic technology of the aforesaid said application in that it demonstrates the first successful production of unfused heterologous protein in *B. subtilis* in which only the desired unfused form of the heterologous protein is produced by the bacteria, and no extraneous amino acids coded for by sources other than the heterologous gene, are present in the heterologous gene product.

It is an object of the present invention to provide an improved method for producing heterologous protein by *B. subtilis*.

Another object of the invention is to provide an improved method for producing a predetermined protein through expression by *B. subtilis*, such protein being non-indigenous to *B. subtilis*.

Another object of the invention is to provide a method for producing protein by *B. subtilis* where the protein is non-indigenous or heterologous to the host species, and is produced as a single unfused peptide having no extraneous amino acids, coded for by sources other than the heterologous gene, attached to the heterologous protein.

Other objects of the invention will become apparent to those skilled in the art from the following description, taken in connection with the accompanying drawings wherein:

BRIEF DESCRIPTION OF THE DRAWINGS

FIG. 1 is a diagram of the human fibroblast interferon gene sequence;

FIG. 2 is a diagram of the nucleotide sequence comprising the regulatory region of the *B. licheniformis* Pen P gene; and FIG. 3 is a diagram of the nucleotide sequence comprising the regulatory sequence fragment from the *B. licheniformis* Pen P gene used to express the human fibroblast interferon gene.

DETAILED DESCRIPTION OF THE INVENTION

Very generally, and in accordance with the invention, a predetermined single protein which is non-indigenous or heterologous to *B. subtilis* is produced through expression by *B. subtilis*. Growth media and conditions are provided for growing a strain of *B. subtilis* in which a plasmid has been introduced. The plasmid is capable of being replicated in the strain or is capable of being integrated into the bacterial chromosome. Such a plasmid carries a heterologous gene that codes for the desired predetermined protein. The heterologous gene contains its own translational initiation codon sequence. This translational initiation codon can be naturally present on the heterologous gene or can be placed there synthetically. Appropriate transcriptional and translational regulatory signals, including operator, promoter and ribosomal binding site sequences, from a source other than the heterologous gene, are also present in the plasmid. The heterologous gene, containing its own translational initiation codon sequence, is located on the plasmid behind a ribosomal binding site sequence at a distance sufficient to provide the spacer nucleotides necessary for proper translation of the heterologous gene. There are no translational initiation codon sequences on the plasmid between the regulatory signals and the point at which the heterologous gene is located. Thus, although the heterologous gene is under the control of plasmid regulatory signals, the presence of the translational initiation codon sequence on the heterologous gene insures that the desired initiation of translation will begin at the site of the heterologous gene. As a result, the heterologous gene is expressed as a single unfused peptide. The heterologous gene product will accumulate in the host organism as an intracellular protein unless the heterologous gene contains its translation initiation codon sequence at the start of its own leader or transport signal peptide sequences. In the latter case, due to the presence of the leader peptide, the heterologous gene product can be secreted by the host organism. Whether it accumulates within the host organism or is secreted, the heterologous gene product can be recovered by means known to the art.

The following examples illustrate ways in which the invention may be employed, but are not intended to limit the scope of the invention.

EXAMPLE 1

The human fibroblast interferon gene has been expressed in *B. subtilis* as a single unfused intracellular protein. The human fibroblast interferon gene for such expression was isolated by means known to the art. See Taniguchi et al, *Proc. Jan. Acad.* 855:464 (1979). More specifically, the human fibroblast interferon cDNA clone, 4E1, was obtained by reverse-transcriptase synthesis of cDNA using human mRNA as template and oligo-dT as primer. The cDNA was made double stranded by the action of *E. coli* DNA polymerase I and nicked with S1-nuclease. Homopolymeric tails were added to the 3'-terminal of the dscDNA by the enzyme terminal-transferase using dCTP as substrate. Similar dG homopolymeric tails were added to the 3'-termini of the plasmid pBR322 which had been linearized at the PstI site. The vector and the dscDNA were hybridized and transformed into *E. coli* K12 cells. The clone, 4E1, was identified by Grunstein-Hogness colony hybridization screens using a p32-labeled probe and further characterized by restriction enzyme analysis. Such analysis shows that PstI digestion of 4E1 yields two insert fragments of about 600 bp and 200 bp, in addition to a fragment corresponding to linear pBR322. BglII, PstI digestion of the same clone shows that the 600 PstI insert fragment can be further digested with BglII to yield two fragments of sizes 358 bp and 200 bp. HinfI digestion of clone 4E1 shows that there are at least three HinfI sites in the insert fragment which generates the three new fragments now present in pBR322.

With the aid of restriction mapping data it was possible to obtain the complete nucleotide sequence of the entire human interferon gene. The translated mature protein sequence of the human fibroblast interferon gene is shown in FIG. 1.

Prior to its expression in *B. subtilis*, the human fibroblast interferon gene was subcloned for expression in *E. coli*. To accomplish this, the human fibroblast interferon gene coding sequence was subcloned by using a synthetic oligonucleotide primer (TATGAGCTACAAC) and the enzyme DNA polymerase I to degrade DNA sequences 5' to the ATG codon that codes for the amino-terminal methionine of the mature interferon. The repaired DNA was then subcloned into pBR322 at the repaired HindIII and at the BamH1 sites. The BglII site in the human interferon gene, just past the UGA translation termination codon, was used to ligate with the BamH1 cohesive end in pBR322 to regenerate an XhoII site. The repaired 5'-terminus of the human interferon gene was blunt-end ligated to the repaired HindIII site; because the original primer has an extra thymidine nucleotide at its 5'-terminus, the HindIII site was regenerated. The resulting clone pβ1-25 was confirmed by restriction analysis and DNA sequence analysis.

A bacillus penicillinase (β-lactamase) promoter was used to express the human fibroblast interferon in *B. subtilis*. The bacillus penicillinase (β-lactamase) promoter fragment was generated from a cloned penicillinase gene. Gray and Chang, J. Bacteriol. 145:422 (1981). The coding sequence of the Pen gene was digested at the PstI site. Then the linearized DNA was trimmed with BAL-31 exonuclease to remove the coding region just beyond the ATG codon. The coding sequence is outlined in FIG. 2. The DNA was then further digested at the EcoRI site located at the 5' end, and repaired by DNA polymerase to generate a blunt-ended fragment. This fragment was further fractionated and purified on acrylamide gel. The purified DNA containing the Pen gene promoter was then cloned into pLL10 at the SmaI site by blunt-end ligation. See Wu, (Editor) *Methods in Enzymology*, 68:98 (1979). Since the SmaI site is flanked by two BamH1 sites, it was possible to excise the promoter fragment by BamH1 digestion. One plasmid designated as pDH5268, which carries a 262 bp insert, was further characterized by sequencing analysis. Such analysis showed that this plasmid contained the complete promoter sequence as shown in FIG. 3.

In order to express the human fibroblast interferon gene in *B. subtilis*, the *E. coli* pβ1-25 plasmid was first converted to a bifunctional replicon by in vitro ligation with bacillus plasmid pOG1196 at the PvuII site. The BamH1 fragment containing the 262 bp Pen promoter was then cloned into the HindIII site 5' to the human fibroblast interferon coding sequence following limited S1 nuclease digestion and *E. coli* DNA polymerase repair. One resulting clone, pDH1151 was further characterized by restriction enzyme analysis. Such analysis showed that in addition to the Bacillus vector, this plasmid carried only sequences derived from *E. coli* plasmid pBR322, the nucleotide sequences coding for mature human fibroblast interferon, and the Pen promoter. Plasmid pDH1151 was then transformed into the *B. subtilis* HV1 host strain BGSC1S53. On the basis of antiviral assay data it was shown that the resulting strain produces intracellular human fibroblast interferon that exhibits antiviral activity comparable to that shown by single unfused mature human fibroblast interferon.

EXAMPLE 2

The eukaryotic pre-insulin gene can be expressed in *B. subtilis* as a single unfused protein which can be secreted by the host organism. As is well known, many proteins, especially in eukaryotic cells, are transported across membranes by means of leader peptides. These leader peptides are usually coded for by the gene coding for the transported protein. The gene coding for eukaryotic pre-insulin contains such leader peptide sequences. The translational codon sequence for pre-insulin is located at the beginning of the leader peptide sequences. As a result, the pre-insulin is expressed with its leader peptide. Due to the presence of the leader peptide, pre-insulin can be transported across cellular membranes. Knowing this, and following the teachings of this invention, eukaryotic pre-insulin can be expressed in *B. subtilis* as a single unfused protein which can be secreted by the host organism. More specifically, in this example, the eukaryotic pre-insulin gene is the heterologous gene of the instant invention. The pre-insulin gene contains its own translational initiation codon sequence located at the beginning of its leader peptide sequences. As in the disclosure and in Example 1, again appropriate transcriptional and translational regulatory signals, including operator, promoter and ribosomal binding site sequences, from a source other than the heterologous pre-insulin gene, are present in the plasmid. The pre-insulin gene is inserted so as to be located on the plasmid behind a ribosomal binding site sequence at a distance sufficient to provide the spacer nucleotides necessary for proper translation of the pre-insulin gene. Again, as in Example 1, there can be no translational initiation codon sequences on the plasmid between the regulatory signals and the point at which the pre-insulin gene is inserted. Thus, although the pre-insulin gene under the control of plasmid regulatory signals the presence of the translational initiation codon sequence on the pre-insulin gene insures that the desired initiation of translation will begin at the site of the pre-insulin gene. As a result, pre-insulin is expressed as a single unfused peptide having its own leader sequence but no extraneous amino acids coded for by bacterial DNA. Due to the presence of the leader peptide, pre-insulin can be secreted by the *B. subtilis* host.

It may be seen, therefore, that the invention provides a method and a vector for the expression of heterologous cloned genes as single unfused proteins in *B. subtilis*. These unfused heterologous proteins will not contain any extraneous amino acids coded for by DNA originating in either the host or the plasmid. These single unfused protein products will accumulate within the host organism, unless the heterologous gene codes for its own leader peptide. In the latter case, the protein products may be secreted by the host organism. Whether they accumulate within the host organism or are secreted, the heterologous gene products can be recovered by means known to the art.

Various modifications of the invention in addition to those shown and described herein will become apparent to those skilled in the art from the foregoing description and accompanying drawings. Such modifications are intended to fall within the scope of the appended claims.

REFERENCES

1. Hori and Osawa, PNAS, (USA) 76:381-385 (1979).
2. Taniguchi et al, Proc. Jan. Acad. 855:464 (1979).
3. Wu, (Editor) Methods in Enzymology, 68:98 (1979).

What is claimed is:

1. A method for intracellularly producing a predetermined protein comprising providing *B. subtilis* bacteria containing at least one plasmid capable of replication in *B. subtilis* or capable of integrating into the bacterial chromosome thereof, the predetermined protein encoded by a heterologous gene in said plasmid, said heterologous gene comprising a translation initiation codon, said heterologous gene under transcriptional and translational regulatory control of a DNA sequence indigenous to *Bacillus licheniformis* which provides said transcriptional and translational regulatory control in *B. subtilis* culturing said *B. subtilis*, intracellularly accumulating unfused predetermined protein in said *B. subtilis*, and recovering said accumulated unfused predetermined protein from said *B. subtilis*.

2. A method according to claim 1 wherein said DNA sequence indigenous to *B. licheniformis* providing transcriptional and translational regulatory control comprises the functional promoter of *B. licheniformis* penicillinase.

3. A method according to claim 1 wherein said predetermined protein is a eukaryotic protein.

4. A method according to claim 1 wherein said predetermined protein is a mammalian protein.

5. A method according to claim 1 wherein said predetermined protein is human fibroblast interferon.

6. A method for creating a microorganism capable of producing a predetermined protein through expression intracellularly comprising forming a plasmid capable of replicating in *B. subtilis* or capable of integrating into the *B. subtilis* bacterial chromosome, said plasmid having a heterologous gene therein coding for a predetermined protein from a source other than *B. licheniformis*, said heterologous gene comprising a translation initiation codon under the transcriptional and translational regulatory control of a DNA sequence indigenous to *B. licheniformis* which provides said transcriptional and translational regulatory control in *B. subtilis* , further there being absent any functional translation initiation codon 5' of said heterologous gene and 3' of said DNA sequence, and introducing said plasmid into B. subtilis.

7. A method according to claim 6 wherein said protein is a eukaryotic protein.

8. A method according to claim 6 wherein said protein is a mammalian protein.

9. A method according to claim 6 wherein said protein is human fibroblast interfreon.

10. A microorganism capable of intracellularly producing a predetermined protein through expression comprising a *B. subtilis* microorganism having therein a plasmid capable of replication in *B. subtilis* or capable of integrating into the B. subtilis bacterial chromosome, said plasmid having a heterologous gene therein coding for a predetermined protein from a source other than *B. licheniformis*, said heterologous gene comprising a translational initiation codon under the transcriptional and translational regulatory control of a DNA sequence indigenous to *B. licheniformis* which provides said transcriptional and translational regulatory control in *B. subtilis*, further there being absent any functional translation initiation codon 5' of said heterologous gene and 3' of said DNA sequence.

11. A microorganism according to claim 10 wherein said predetermined protein is a eukaryotic protein.

12. A microorganism according to claim 10 wherein said predetermined protein is a mammalian protein.

13. A microorganism according to claim 10 wherein said predetermined protein is human fibroblast interferon.

14. A transformant bacterial culture consisting essentially of microorganisms having therein a plasmid capable of replication in *B. subtilis* or capable of integrating into the *B. subtilis* bacterial chromosome, said plasmid having a heterologous gene therein coding for a predetermined protein from a source other than *B. licheniformis*, said heterologous gene comprising a translational initiation codon under the transcriptional and translational regulatory control of a DNA sequence indigenous to *B. licheniformis* which provides said transcriptional and translational regulatory control in *B. subtilis* , further there being absent any functional translation initiation codon 5' of said heterologous gene 3' of said DNA sequence.

15. A plasmid capable of replication in *B. subtilis* or capable of integrating into the *B. subtilis* bacterial chromosome, said plasmid having a heterologous gene therein coding for a predetermined protein from a source other than *B. licheniformis*, said heterologous gene comprising a translation initiation codon under the transcriptional and translational regulatory control of a DNA sequence indigenous to *B. licheniformis* which provides said transcriptional and translational regulatory control in *B. subtilis*, further there being absent any functional translation initiation codon 5' of said heterologous gene and 3' of said DNA sequence.

16. The plasmid of claim 15 wherein said DNA sequence indigenous to B. licheniformis providing transcriptional and translational regulatory control comprises the functional promoter of *B. licheniformis* penicillinase.

17. A plasmid according to claim 15 wherein said predetermined protein is a eukaryotic protein.

18. A plasmid according to claim 15 wherein said predetermined protein is a mammalian protein.

19. A plasmid according to claim 15 wherein said predetermined protein is human fibroblast interferon.

* * * * *